(12) United States Patent
Burstein et al.

(10) Patent No.: US 9,119,642 B2
(45) Date of Patent: Sep. 1, 2015

(54) JOINT REPLACEMENT SPACERS

(71) Applicants: Albert H. Burstein, Reno, NV (US); Jonathan T. Deland, New York, NY (US)

(72) Inventors: Albert H. Burstein, Reno, NV (US); Jonathan T. Deland, New York, NY (US)

(*) Notice: Subject to any disclaimer, the term of this patent is extended or adjusted under 35 U.S.C. 154(b) by 0 days.

(21) Appl. No.: 14/620,651

(22) Filed: Feb. 12, 2015

(65) Prior Publication Data

US 2015/0190152 A1    Jul. 9, 2015

Related U.S. Application Data

(62) Division of application No. 13/834,361, filed on Mar. 15, 2013.

(51) Int. Cl.
| | |
|---|---|
| *A61F 2/42* | (2006.01) |
| *A61B 17/17* | (2006.01) |
| *A61B 17/16* | (2006.01) |
| *A61B 17/56* | (2006.01) |
| *A61F 2/30* | (2006.01) |

(52) U.S. Cl.
CPC .............. *A61B 17/17* (2013.01); *A61B 17/1615* (2013.01); *A61B 17/1637* (2013.01); *A61B 17/1662* (2013.01); *A61B 17/1682* (2013.01); *A61B 17/1739* (2013.01); *A61B 17/562* (2013.01); *A61F 2/4225* (2013.01); *A61B 2017/1602* (2013.01); *A61B 2017/1775* (2013.01); *A61B 2218/00* (2013.01); *A61F 2002/30301* (2013.01); *A61F 2002/30878* (2013.01); *A61F 2002/4238* (2013.01)

(58) Field of Classification Search
CPC ....... A61F 2/42; A61F 2/4225; A61F 2/4202; A61F 2/4241; A61F 2/4261; A61F 2/4606; A61F 2/4605; A61F 2002/42; A61F 2002/4202; A61F 2002/4238–2002/4297
USPC .......... 623/21.11–21.18, 18.11, 16.11, 14.12, 623/20.11, 20.33, 20.29, 20.3
See application file for complete search history.

(56) References Cited

U.S. PATENT DOCUMENTS

| | | | | |
|---|---|---|---|---|
| 3,872,519 | A * | 3/1975 | Giannestras et al. ...... | 623/21.18 |
| 3,886,599 | A * | 6/1975 | Schlein ...................... | 623/21.18 |
| 3,975,778 | A * | 8/1976 | Newton, III ............... | 623/21.18 |
| 4,021,864 | A * | 5/1977 | Waugh ........................ | 623/21.18 |
| 4,069,518 | A * | 1/1978 | Groth et al. ................ | 623/21.18 |
| 4,156,944 | A * | 6/1979 | Schreiber et al. .......... | 623/21.18 |
| 4,198,712 | A * | 4/1980 | Swanson ..................... | 623/21.14 |
| D290,877 | S * | 7/1987 | Giampapa et al. .......... | D24/155 |
| D290,879 | S * | 7/1987 | Giampapa et al. .......... | D24/155 |
| D291,248 | S * | 8/1987 | Sugarbaker et al. ........ | D24/155 |
| 4,936,860 | A * | 6/1990 | Swanson ..................... | 623/21.14 |
| 5,766,259 | A * | 6/1998 | Sammarco ................... | 623/21.18 |
| 5,824,106 | A * | 10/1998 | Fournol ...................... | 623/21.18 |
| 6,168,630 | B1 * | 1/2001 | Keller et al. ............... | 623/21.11 |
| 6,183,519 | B1 * | 2/2001 | Bonnin et al. ............. | 623/21.18 |
| 7,025,789 | B2 * | 4/2006 | Chow et al. ................ | 623/21.11 |
| 7,025,790 | B2 * | 4/2006 | Parks et al. ................ | 623/21.18 |
| 7,160,329 | B2 * | 1/2007 | Cooney et al. ............. | 623/20.11 |
| 7,182,787 | B2 * | 2/2007 | Hassler et al. ............. | 623/21.15 |
| 7,534,270 | B2 * | 5/2009 | Ball .......................... | 623/21.18 |
| 7,628,819 | B2 * | 12/2009 | Gupta et al. ............... | 623/21.11 |
| D619,718 | S * | 7/2010 | Gannoe et al. ............. | D24/155 |
| 7,766,970 | B2 * | 8/2010 | Shultz et al. ............... | 623/21.14 |
| 7,819,924 | B2 * | 10/2010 | VanDer Meulen et al. ........................... | 623/21.11 |
| D642,689 | S * | 8/2011 | Gannoe et al. ............. | D24/155 |

(Continued)

*Primary Examiner* — Alvin Stewart
(74) *Attorney, Agent, or Firm* — Foley Hoag LLP

(57) ABSTRACT

Devices and methods are disclosed for joint replacement.

19 Claims, 13 Drawing Sheets

(56) References Cited

U.S. PATENT DOCUMENTS

| | | | |
|---|---|---|---|
| 8,052,755 B2* | 11/2011 | Naidu | 623/21.12 |
| 8,066,777 B2* | 11/2011 | Palmer et al. | 623/21.14 |
| 8,088,168 B2* | 1/2012 | Hassler et al. | 623/21.12 |
| 8,118,876 B2* | 2/2012 | Gupta et al. | 623/21.11 |
| 8,333,806 B2* | 12/2012 | Scheker | 623/21.13 |
| 8,617,175 B2* | 12/2013 | Park et al. | 606/89 |
| 8,668,743 B2* | 3/2014 | Perler | 623/21.18 |
| 8,758,445 B2* | 6/2014 | Gupta et al. | 623/21.11 |
| 2006/0036330 A1* | 2/2006 | Shultz et al. | 623/21.12 |
| 2006/0142870 A1* | 6/2006 | Robinson et al. | 623/21.18 |
| 2007/0055381 A1* | 3/2007 | Berelsman et al. | 623/21.12 |
| 2007/0173947 A1* | 7/2007 | Ratron et al. | 623/21.18 |
| 2007/0185582 A1* | 8/2007 | Palmer et al. | 623/21.12 |
| 2008/0027558 A1* | 1/2008 | Palmer et al. | 623/21.12 |
| 2009/0182433 A1* | 7/2009 | Reiley et al. | 623/18.11 |
| 2009/0204224 A1* | 8/2009 | Berelsman et al. | 623/21.14 |
| 2009/0254190 A1* | 10/2009 | Gannoe et al. | 623/21.11 |
| 2009/0319050 A1* | 12/2009 | Palmer et al. | 623/21.12 |
| 2010/0010636 A1* | 1/2010 | Shultz et al. | 623/21.12 |
| 2010/0057216 A1* | 3/2010 | Gannoe et al. | 623/21.18 |
| 2010/0280625 A1* | 11/2010 | Sanders et al. | 623/21.18 |
| 2011/0125275 A1* | 5/2011 | Lipman et al. | 623/20.11 |
| 2011/0208317 A1* | 8/2011 | Feldman | 623/21.18 |
| 2012/0010718 A1* | 1/2012 | Still | 623/21.18 |

* cited by examiner

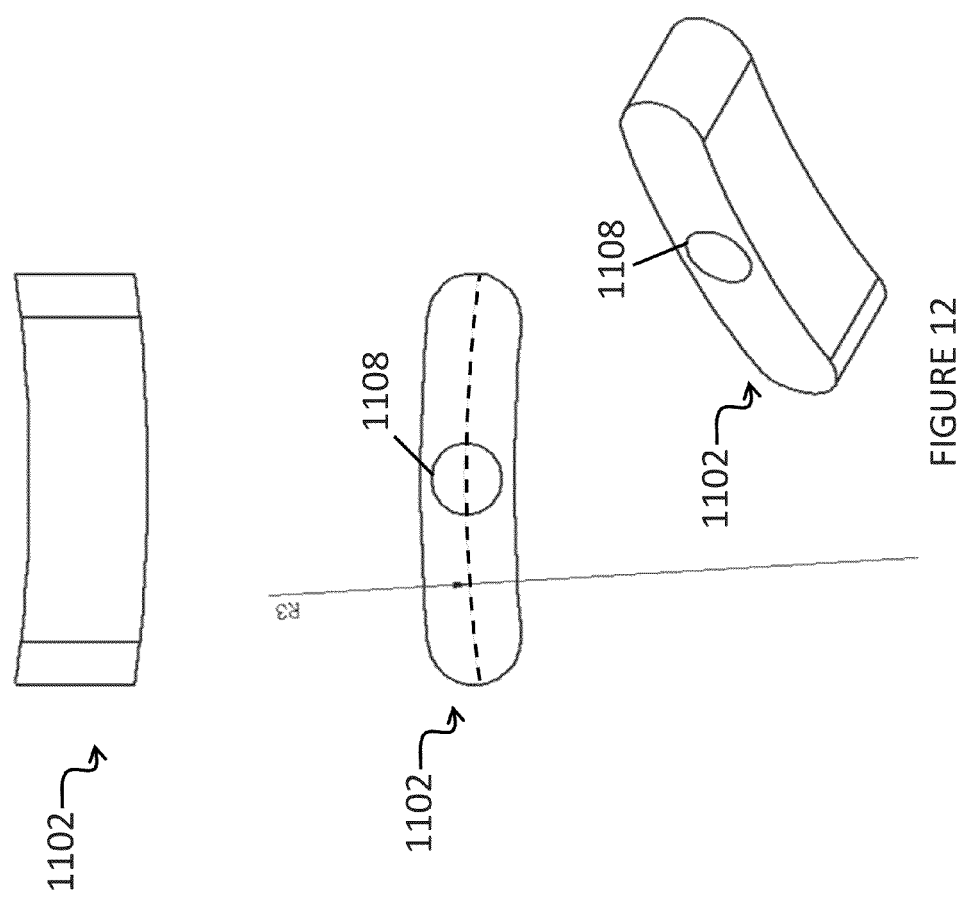

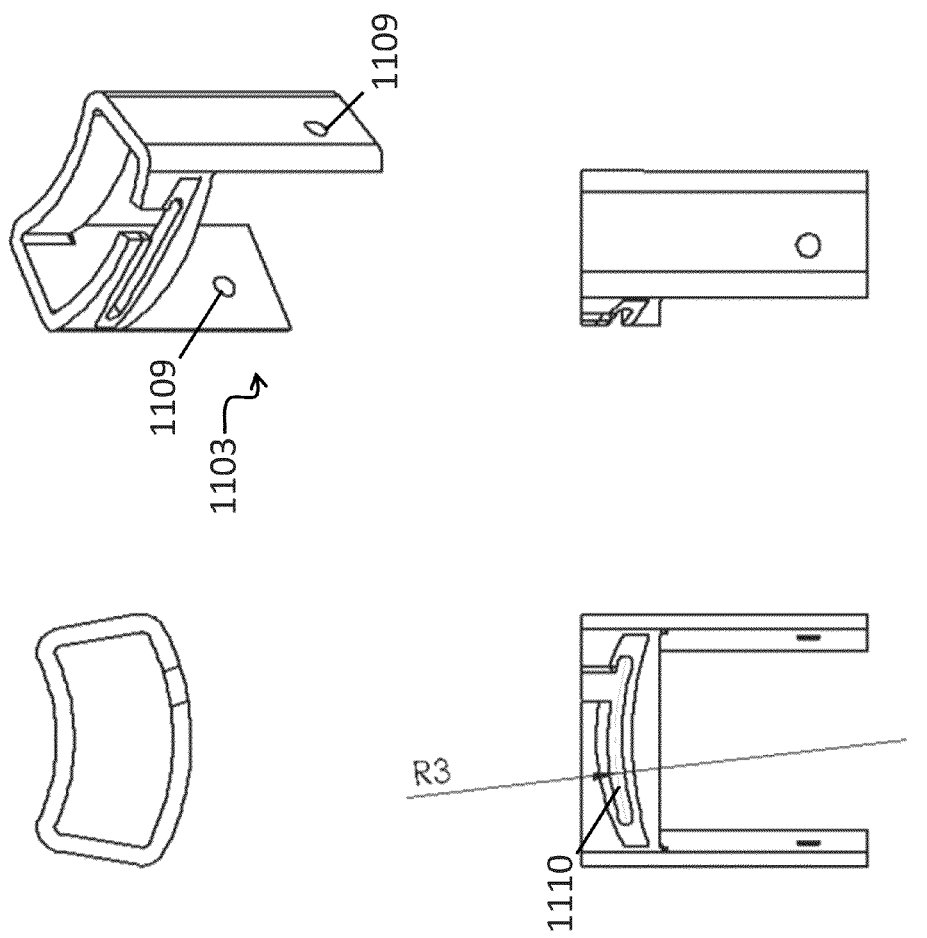

JOINT REPLACEMENT SPACERS

CROSS-REFERENCE TO RELATED APPLICATION

This application claims priority to U.S. patent application Ser. No. 13/834,361, filed 15 Mar. 2013.

SUMMARY

Devices and methods are disclosed for joint replacement.

BRIEF DESCRIPTION OF THE DRAWINGS

FIGS. 11, 12 and 13 schematically show a bit, bushing and mount for shaping a bone to receive a spacer for hemi-joint replacement.

DETAILED DESCRIPTION

Figure 1:
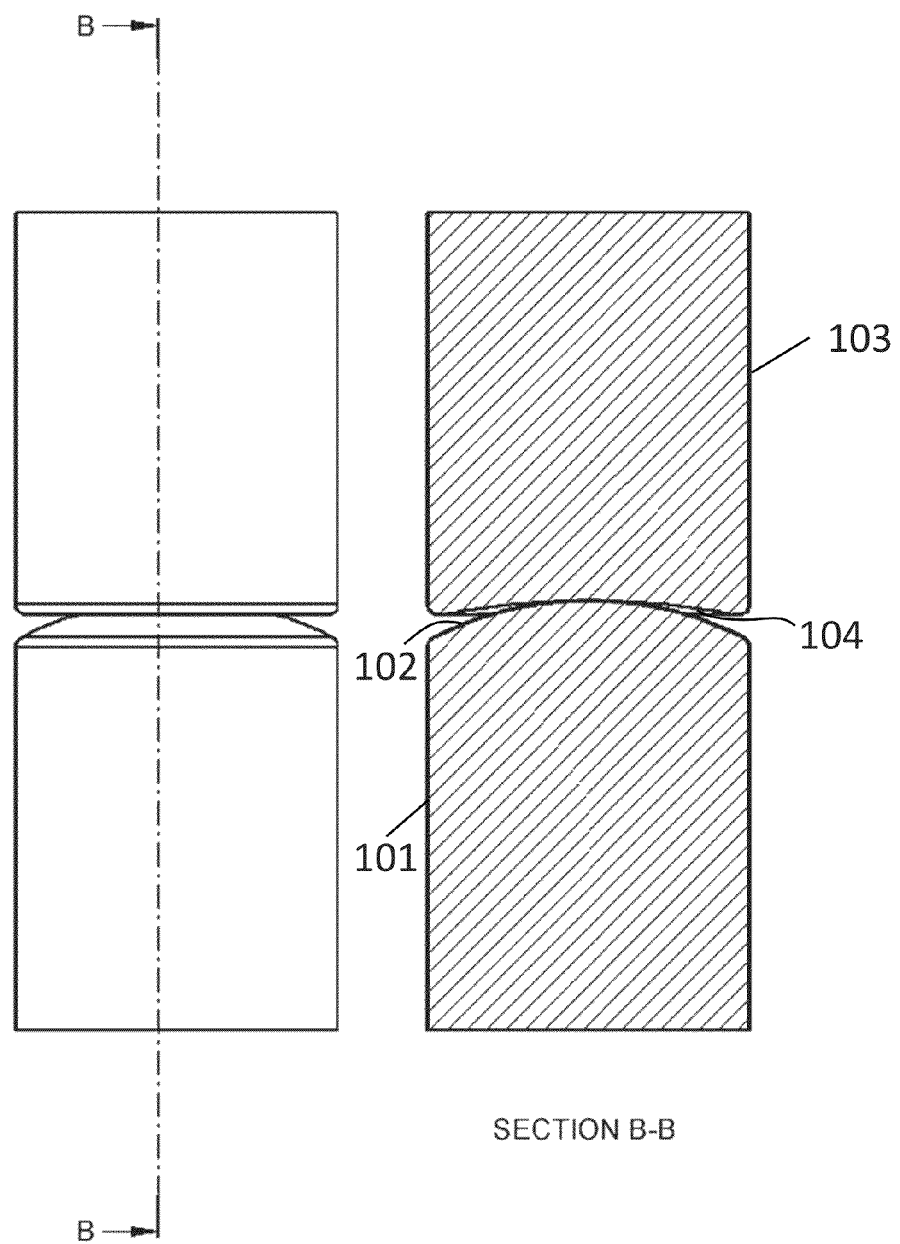
FIG. 1 schematically shows a joint.

A spacer for joint replacement can be used to replace a portion of bone in a joint. Such spacers and methods for using such spacers are described in U.S. Pat. No. 8,303,664, issued Nov. 6, 2012, which is hereby incorporated herein by reference in its entirety. The joint is originally formed by two bones, each having an articulating surface, either of which may have some, all or none of the related cartilage remaining. The joint schematically shown in FIG. 1 includes a first bone 101 with an articular surface 102 meeting a second bone 103 with an articular surface 104. The cartilage is not drawn separately for simplicity, but is meant to be included in each schematically drawn bone, to the extent that cartilage remains. A patient may need to have a portion of the first bone replaced, while the second bone remains relatively healthy with a functional articular surface. In that case, a full joint replacement, in which portions of both bones are removed, is undesirable. Instead, a hemi-joint replacement spacer can be used to replace a portion of the first bone, while leaving the second bone entirely intact. It is desirable to leave as much healthy bone undisturbed as possible. The joint replacement spacer can be designed to interact with the natural articular surface of the second bone, or else to articulate with a prepared surface of the second bone.

A wide variety of combinations of curved elements could be used to generate any particular cut surface so as to be complementary to a spacer. A cut surface can be formed with multiple radii of curvature generated by two or more generators, or "surface-generating curves." Typically the surface-generating curves will be planar. In some embodiments, a cutting bit will include two different radii of curvature on the cutting surface and a third radius of curvature will be introduced by translating or rotation the bit through another curve, located on either a collar or on a cutting guide. In some embodiments a cutting burr will generate a single radius of curvature while other curves and radii of curvature are generated by the collar, or by the guide, or by both the collar and the guide. One of skill in the art will recognize that many different combinations of generators are possible, and any system that generates the necessary three (or four, or more) radii of curvature would suffice. Some radii of curvature will be infinite, meaning that at least a portion of some generating curves may be flat.

Several examples are shown schematically in the figures and are described below.

Figure 2:
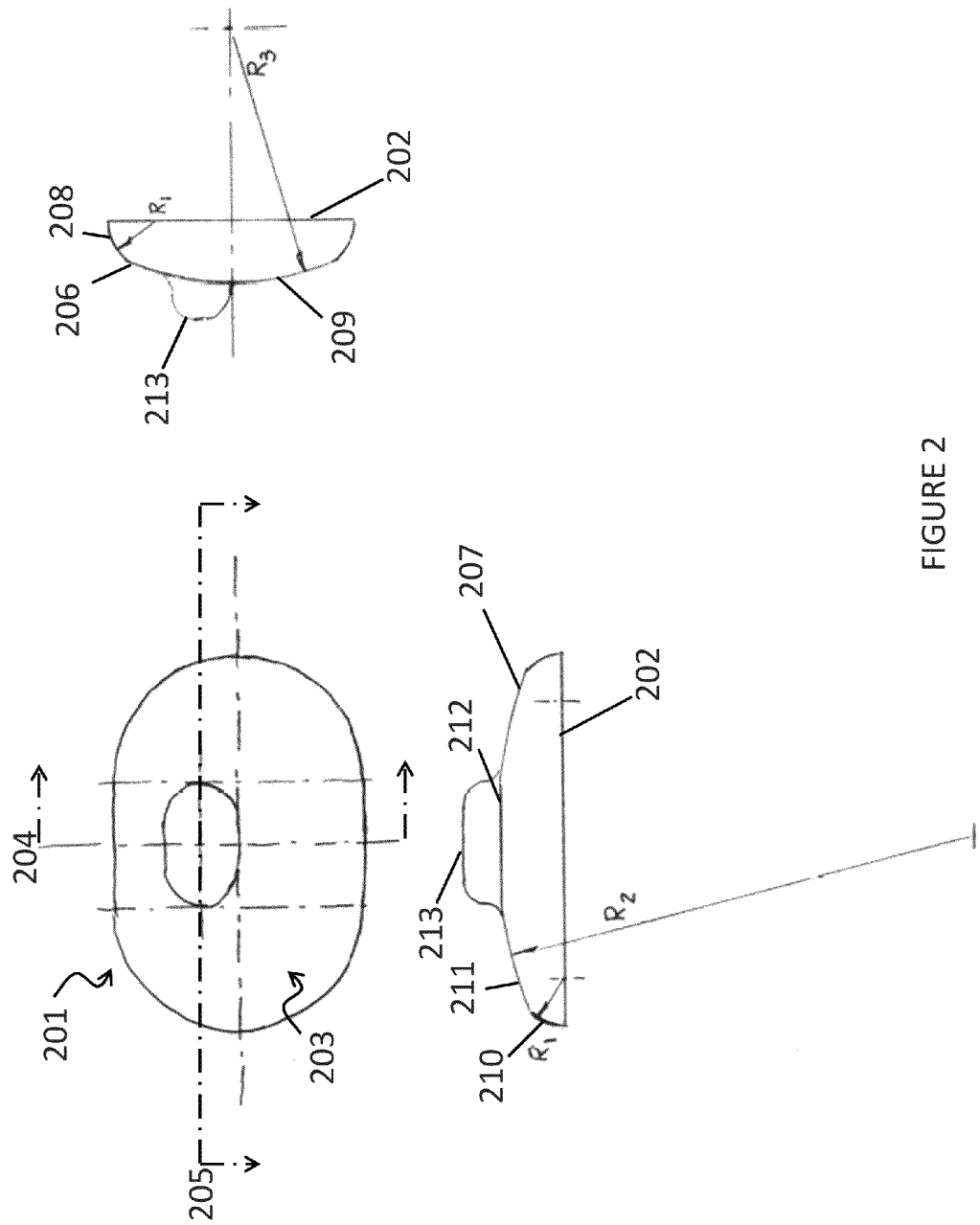
FIG. 2 schematically shows a spacer for hemi-joint replacement.

FIG. 2 schematically shows a hemi-joint replacement spacer 201. The spacer 201 has an articulating surface 202 for (a) replacing the articular surface of a first bone, and (b) articulating with a second bone. In reality, the articulating surface 202 would probably not be substantially flat as shown, but would rather be curved to mimic the removed articular portion of the first bone. The spacer 201 also has a secondary surface 203, at least part of which, or in some cases all of which, is a stabilizing surface sized and shaped to fit against a cut surface of the first bone. The cut surface can be prepared so as to be generally complementary to the stabilizing surface. In contrast to joint implants that are affixed to the bone by an interference fit, a surface to allow ingrowth, cement, screws, or the like, when the spacer 201 is in place on the cut surface of the first bone, the spacer is allowed a small amount of movement relative to the bone. It is the interaction of the stabilizing surface and the cut surface of the first bone that generally stabilizes the spacer relative to the first bone without completely immobilizing the spacer relative to the first bone.

FIG. 2 shows that the spacer can have a first axis 204 and a second axis 205. The two axes may be perpendicular to one another, as shown in FIG. 2, or they may be non-perpendicular. One or both axes may be curved. The spacer 201 shown in FIG. 2 has a specific shape in each cross-section perpendicular to the axes. In each cross-section, the spacer 201 defines a curve 206, 207. The first curve 206 has first and second portions 208, 209 that have non-equal radii of curvature shown as $R_1$ and $R_3$ respectively. The second curve 207 has third and fourth portions 210, 211 that have non-equal radii of curvature shown as $R_1$ and $R_2$ respectively. Although FIG. 2 shows the first and third portions having the same radius of curvature, $R_1$, in some embodiments the first and third portions may have non-equal curvatures. In the pictured embodiment, the radius of curvature of the first and third portions, $R_1$, is equal to the radius of a circular bone cutting tool, described in more detail below. FIG. 2 also shows that the second curve 207 includes a fifth portion 212. In this case, the fifth portion 212 is flat, i.e. it has zero curvature, or an infinite radius of curvature, but in practice a fifth portion could have any radius of curvature. In this case, the spacer also includes a bump 213, which is an optional feature of the stabilizing surface. When using a spacer 201 that includes a bump 213, after forming the cut surface with the complementary radii of curvature, a cavity will also need to be formed complementary to the bump 213.

The spacer shown in FIG. 2 has a generally convex stabilizing surface, and is designed to be seated on a complementary, concave, prepared surface of the first bone. Alternatively, the stabilizing surface can be generally concave, designed to be seated on a complementary, convex, prepared surface of the first bone. Other possible shapes include the cases where either the second portion or the fourth portion is flat with no curvature (i.e., infinite radius of curvature). Also the stabilizing surface could be saddle-shaped, so that the second portion is concave while the fourth portion is convex, or vice versa. In some saddle-shaped embodiments the radii of curvature of the second and fourth portions may be equal in magnitude, but opposite in sign. In that case the two radii of curvature of the second and fourth portions are considered to be not equal.

Figure 3:
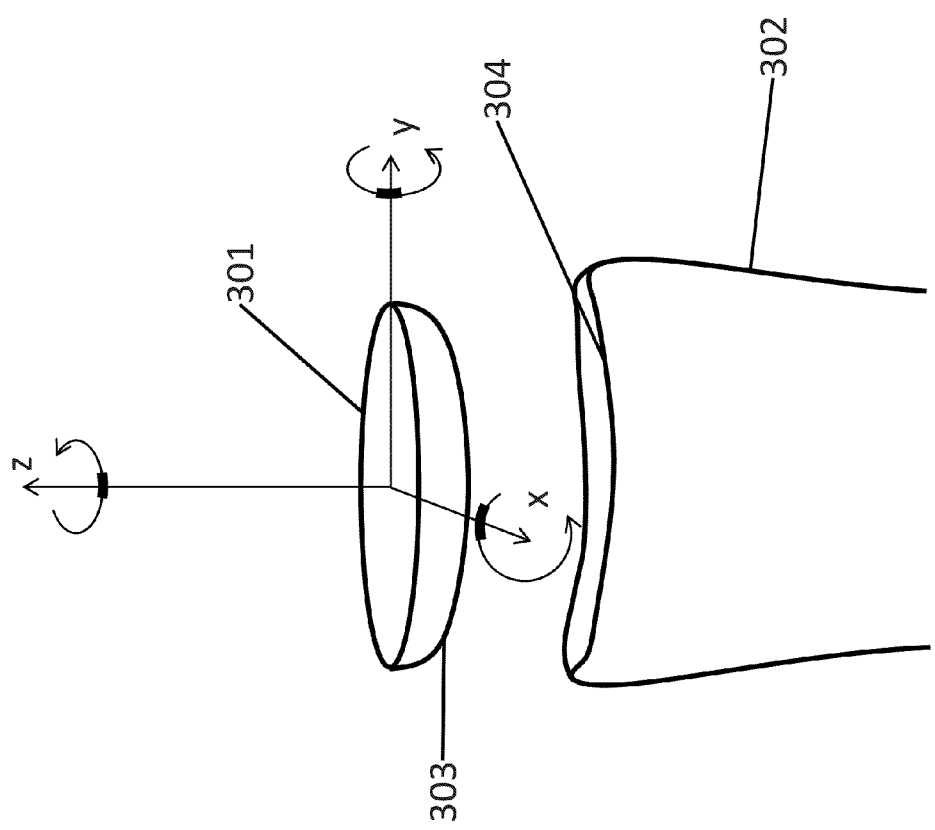
FIG. 3 schematically shows an exploded view of a spacer for hemi-joint replacement positioned in a joint.

As shown in FIGS. 2 and 3, the perimeter of the spacer is generally elliptical. Without altering the relationship of the various portions of the first and second curves, the perimeter could have essentially any shape in the x-y plane shown in FIG. 3, such as a circle, oval, trapezoid, parallelogram, kite, triangle, or any other shape that would help the space to mimic the anatomy of the replaced portion of bone.

FIG. 3 schematically shows the spacer 301 above a bone 302 in an exploded view. The convex stabilizing surface 303 of the spacer 301 is visible along with the concave prepared surface 304 of the bone 302. The spacer is shown oriented in space by a three-dimensional Cartesian coordinate system with axes x, y and z, and with arrows indicating rotation about each of the three axes. Rotation about the x axis is "roll," rotation about y axis is "pitch," and rotation about the z axis is "yaw." In this particular embodiment, the horizontal x and y axes are the first and second axes of spacer.

One property of the spacer 301 shown in FIG. 3 is that, when the stabilizing surface 303 is seated against the prepared surface 304 of the bone 302, the spacer is substantially prevented from yawing, i.e., rotating about the z axis. Because the first and third portions have different radii of curvature, the spacer 301 cannot yaw and remain fully seated against the bone 302; any rotation of the spacer 301 will tend to cause it to ride up off of the prepared surface 304. If the second and fourth portions had equal radii of curvature, the spacer might be able to yaw. But because the second and fourth portions are not equally curved, the aspect of the cut surface that has been shaped to match the second portion cannot also match the fourth portion. Any yawing will therefore tend to cause the spacer 301 to ride up and off of the cut surface 304. To the extent that the reapproximated joint holds the stabilizing surface 303 down onto the cut surface 304, the spacer 301 will be inhibited from yawing. Because the cut surface 304 will never be perfectly complementary, it may be possible for the spacer 301 to yaw slightly, but generally, the mating surfaces will inhibit the spacer 301 from riding up and off the surface 304. Similarly, the fact that the first and second radii of curvature are not equal will tend to prevent the spacer 301 from pitching, or rotating about the y axis. The fact that the third and fourth radii of curvature are not equal will tend to prevent the spacer 301 from rolling, or rotating about the x axis.

Figure 4:
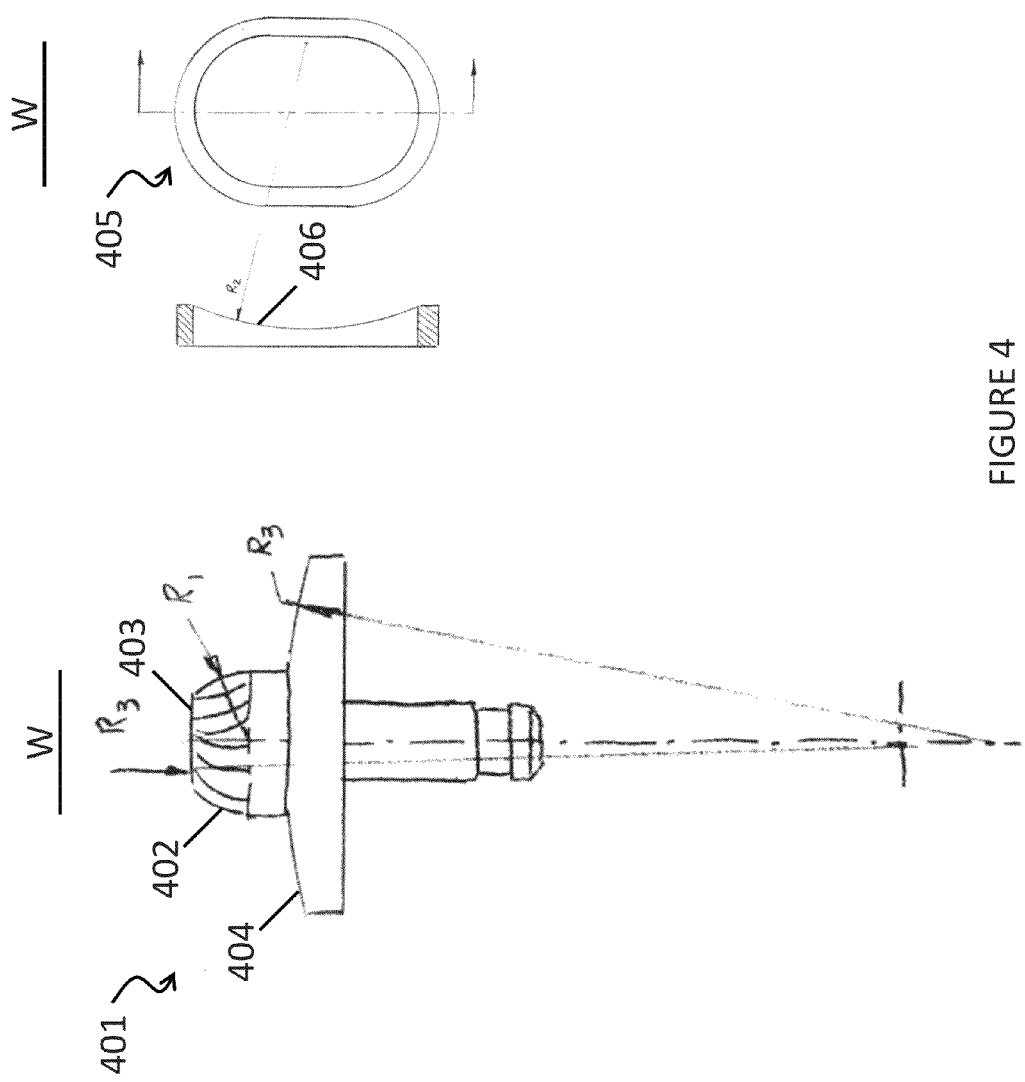
FIG. 4 schematically shows a cutting implement for shaping a bone to receive a spacer for hemi-joint replacement.

FIG. 4 schematically shows a cutting implement, or bit, or burr, 401 useful for removing portions of bone having a defined radius of curvature. The bit is configured to be attached to a powered rotational driver, for example an air driven drill or auger, or any other source or rotational motion. The bit 401 has a rotating cutting blade. One portion 402 of the cutting blade defines a particular first radius of curvature shown as $R_1$. A second portion 403 of the cutting blade defines a radius of curvature shown as $R_3$. The implement 401 also has a collar 404. In this embodiment the collar can also have radius of curvature $R_3$, although in other similar embodiments, the collar could simply be flat. The collar is designed to ride on a guide 405. This particular guide is generally oval shaped, and is intended to be secured to the first bone, positioned directly above the portion of the first bone to be removed. The edge 406 of the guide defines a radius of curvature $R_2$. To form the cut surface, the bit 401 is plunged downward until the collar 404 contacts the curved edge 406. The rotating bit is then swept along the guide 404 so as to form the cut surface on the bone. A cross-section of the resulting surface parallel to the long axis of the guide will have radii of curvature $R_1$ near the edge and $R_2$ in the middle. A cross-section of the resulting surface parallel to the short axis of the guide will have radii of curvature and $R_1$ near the edge and $R_3$ in the middle. Thus, the resulting cut surface will be complementary to a spacer 201 like the one shown in FIG. 2, except for the bump 213. As shown in FIG. 4, the cutting portion 402 of the bit 401 at its widest point has a width marked W which is roughly equal to, or slightly smaller than, the width of the opening in the guide 405, also marked W. In this embodiment, the bit 401 would be plunged downward to meet the guide 405 and then swept back and forth in only one direction.

As an alternative, the bit could be formed as a hemispherical cutting surface with radius of curvature $R_1$ at all points on the cutting surface. In that case, a different part would need to generate the $R_3$ radius of curvature. One possibility would be to make the bit have a width significantly smaller than the inner dimension of the guide 405. Then the user would be free to sweep the bit in two dimensions over the guide. The collar 404 can then be formed with radius of curvature $R_3$ to generate that radius of curvature as the bit is swept along the direction of the short axis of the guide 405.

As shown in FIG. 4, the bit 401 used in combination with the guide 405 would result in a concave prepared surface. As an alternative, the bit 401 and guide 405 could be designed to result in a prepared surface that is convex. The radius of curvature of the collar 404 could be inverted so that the collar is concave with radius of curvature $R_3$. And likewise radius of curvature of the curved edge 406 of the guide 405 could be inverted so as to have a convex radius of curvature $R_2$. In that case, with a concave collar and a convex guide, the resulting prepared surface of the bone would be convex. As still another alternative, both the collar and the guide could be convex, resulting in a saddle-shaped prepared surface. As still another alternative, both the collar and the guide could be concave, resulting in a different saddle-shape for the prepared surface.

FIGS. 2-4 can also be thought of as an example of the more general statement of the properties of the stabilizing surface and complementary cut surface as defined by planar generating curves. In the case where the cutting surface 402, 403 of the bit 401 has two radii of curvature $R_1$ and $R_3$ and the collar 404 is flat, the cutting surface defines one planar generating curve having, in this case, two radii of curvature. That generating curve is combined with the planar generating curve defined by the curved edge of the guide 406. By combining (1) the curve defined by the cutting surface 402, 403 of the bit, and (2) the curved edge of the guide 406, a surface is created. The surface has two geometrically independent aspects, namely the first and second axes 204, 205. Along these geometrically independent aspects, that is, in cross-sections perpendicular to the two axes, the surface has two radii of curvature. In one geometrical aspect, the radius of curvature varies from $R_1$ to $R_2$ and back to $R_1$ so that the radius of curvature is non-constant. In the other aspect, the radius of curvature varies from $R_1$ to $R_3$ and back to $R_1$ so that the radius of curvature is again non-constant in a second geometrical aspect.

"Geometrically independent aspects" is used herein to denote non-congruent axes such that every point on the surface has a unique coordinate with respect to the axes. Examples of geometrically independent aspects include perpendicular linear axes, as shown in FIG. 2, non-perpendicular linear axes, and curvilinear coordinate systems such as cylindrical systems in which one aspect is radial and another is azimuthal, toroidal systems in which radial distance is measured from a circle of fixed radius, and azimuth is measured about the center of the fixed circle, toroidal systems in which the fixed radius of the toroid varies with angle for example elliptical, hyperbolic, or parabolic coordinate systems, etc. In the case of linear axes, a "cross-section" perpendicular to the axis is easy to visualize since it is entirely in a single plane. In the case of a coordinate system with an angular axis, at least one cross-section may be harder to visualize, since it may lie in a more complicated surface, such as a circular, elliptical, parabolic or hyperbolic cylinder, rather than a simple plane as in the case of linear axes. Nonetheless, the intersection of the stabilizing surface with such a geometrical surface defines a type of cross-section and is well-defined. In the case of curvilinear coordinates, the existence of a curve in the coordinate system may constitutes one of the generating curves of the surface.

Figure 5:
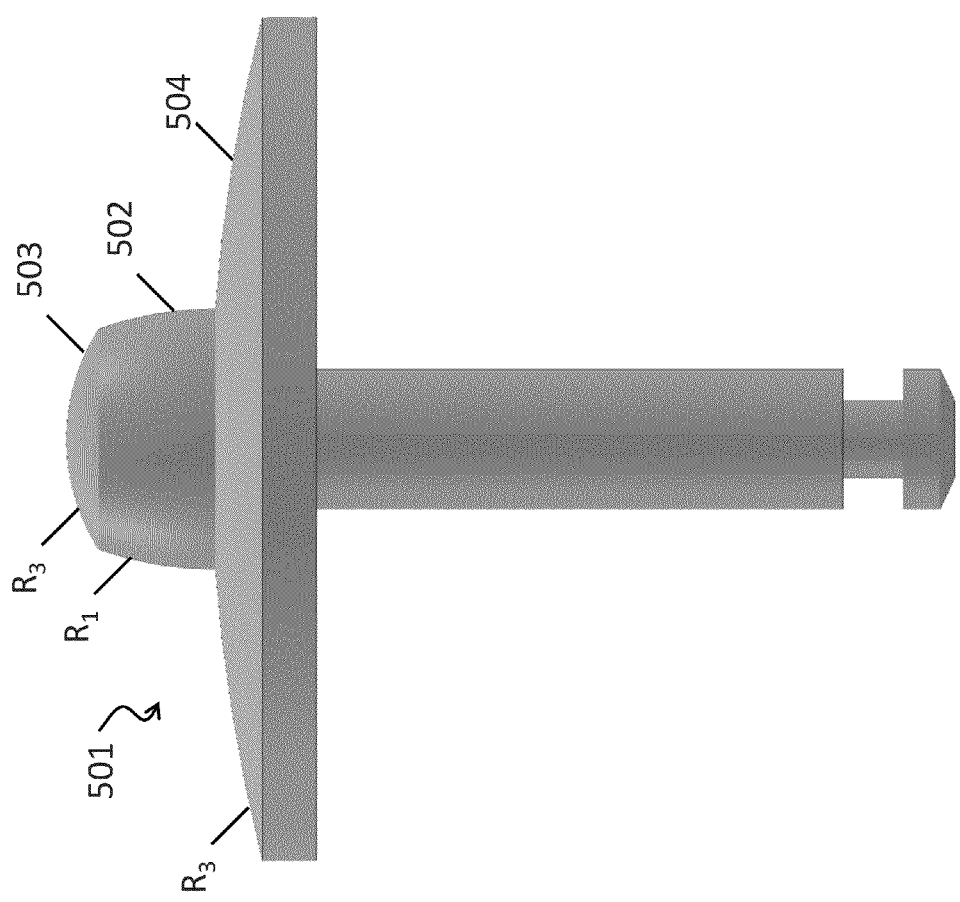
FIG. 5 schematically shows a cutting implement for shaping a bone to receive a spacer for hemi-joint replacement.

FIG. 5 schematically shows a similar bit 501 with a first radius of curvature $R_1$ on the "edge-cutting" portion 502 of the bit 501, and a different radius $R_3$ on the "plunge-cutting" portion 503 of the bit. The collar 504 also has radius of curvature $R_3$. This bit 501 could be used either with a guide whose width matched the width of the widest part of the edge-cutting portion 502, in which case the plunge-cutting portion would entirely generate the aspect of the cut surface having radius of curvature $R_3$ while the bit 501 was swept in only one direction in the guide. Or the bit 501 could be used with a wider guide that allowed the bit 501 to be swept in a second direction, so that both the collar 504 and the plunge-cutting portion 503 define the aspect of the cut surface having radius of curvature $R_3$. In the case where the width of the guide matches the width of the bit, the cutting portion of the bit defines a generating curve with two radii of curvature, while the guide defines another generating curve with a single radius of curvature. The two planar curves combine in the same way described with respect to FIGS. 2-4.

Figure 6:
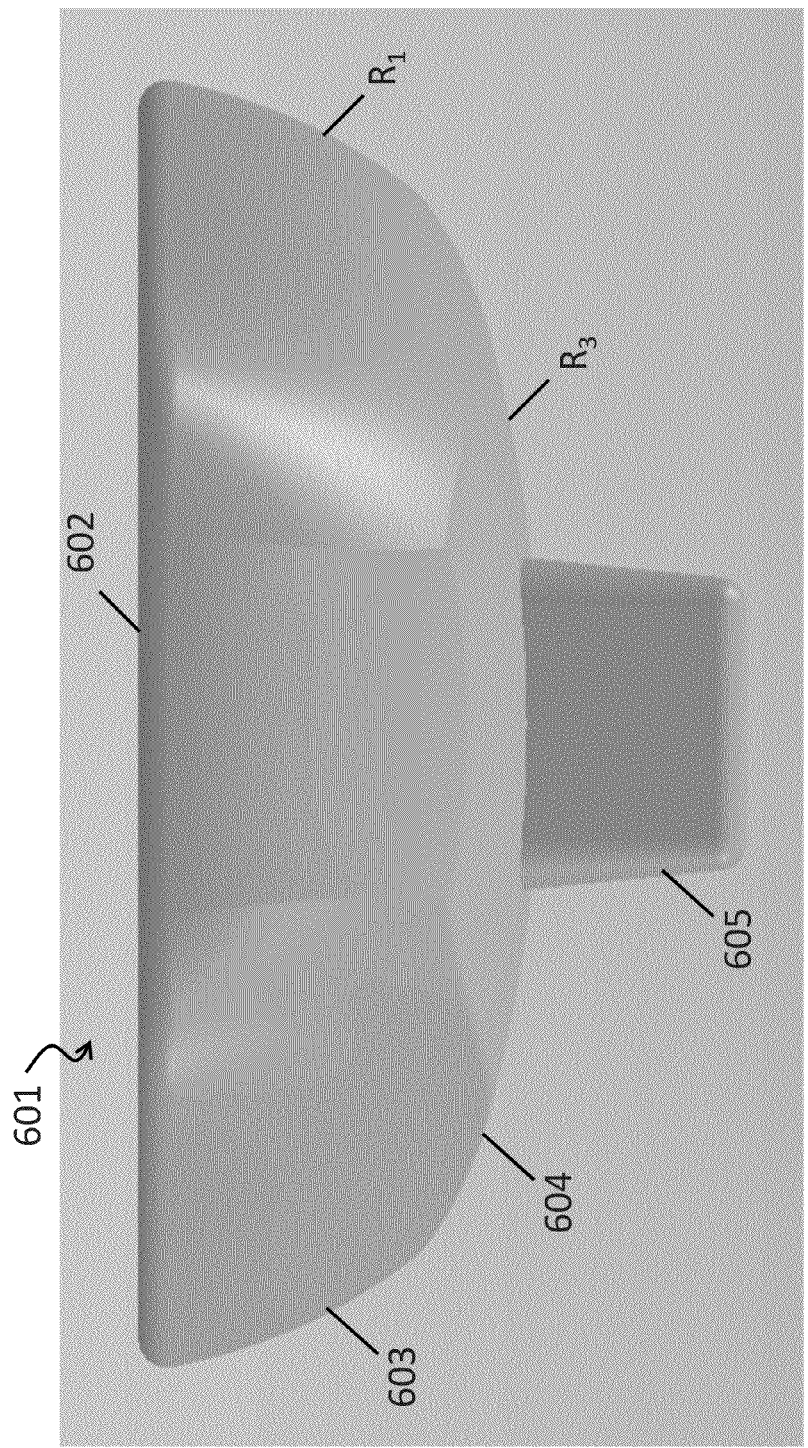
FIG. 6 schematically shows an anterior view of a spacer for hemi-joint replacement in the proximal phalangeal joint.
Figure 7:
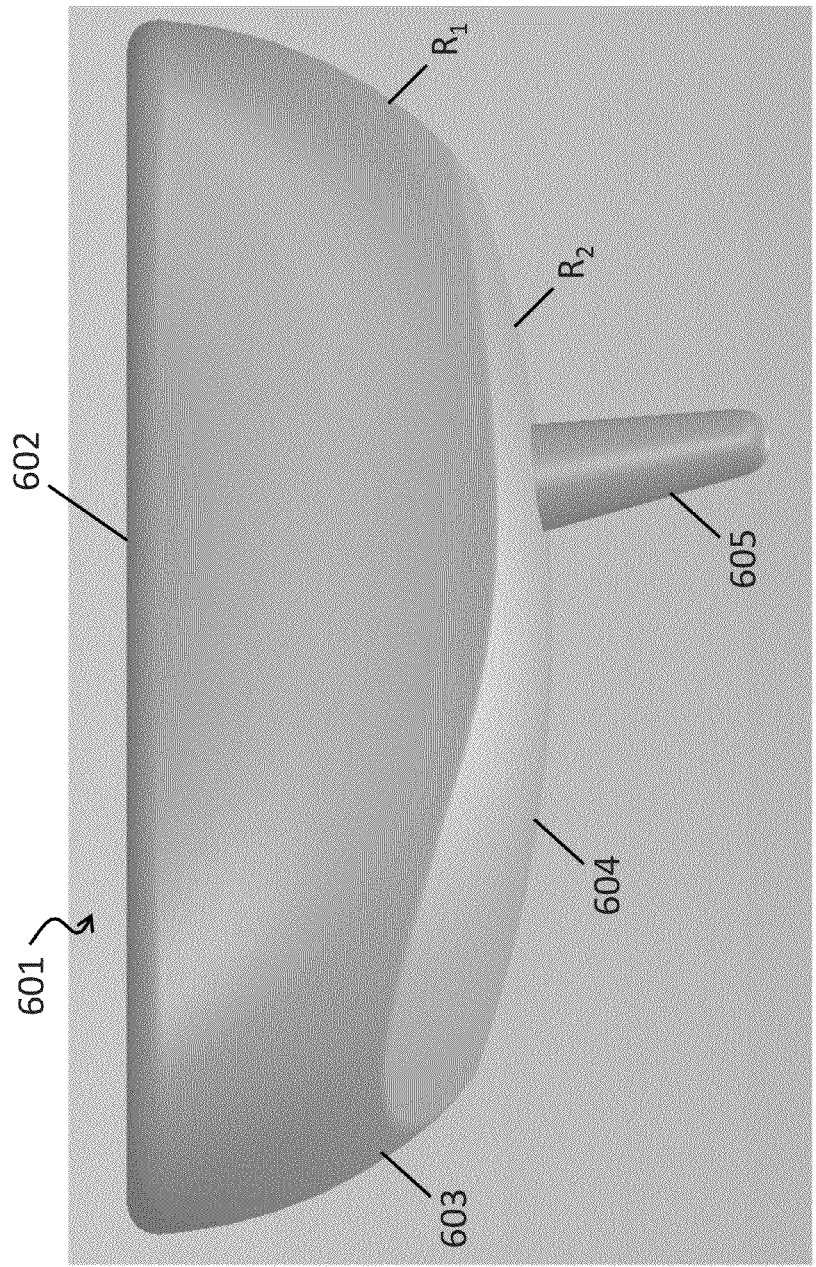
FIG. 7 schematically shows a medial view of a spacer for hemi-joint replacement in the proximal phalangeal joint.

FIG. 6 schematically shows one embodiment of a particular spacer 601. This embodiment is particularly useful in a foot at the metatarsal-phalangeal joint. The articulating surface 602 of the spacer 601 articulates with the metatarsal head and the spacer replaces the proximal articular surface of the proximal phalanx. As implanted in the foot, FIG. 6 presents what would be an anterior view of the spacer 601. The opposite or inferior side of the spacer 601 has an outer edge portion 603 with a first radius of curvature $R_1$. The central portion 604 of the inferior side has a different radius of curvature $R_3$ in this cross-section. FIG. 7 schematically shows the same spacer 601 but in a lateral view. The articular surface 602 is still visible. The edge portion 603 is also still visible showing radius of curvature $R_1$. The central portion 604 is also still visible, but from the lateral direction, the other radius of curvature, $R_2$, is now visible. Inferior or superior views of the spacer 601 would show a generally trapezoidal shape with rounded corners.

The particular embodiment shown in FIGS. 6 and 7 includes an optional stabilizing bump 605. In addition to the stabilizing surface, which is complementary to the prepared bone surface incorporating multiple radii of curvature as explained above, the bump is complementary to a cavity formed on the bone surface. The bump fits inside, but does not entirely fill, the cavity. In this way the bump can allow for some limited motion of the spacer on the prepared surface, to the extent that the bump can move within the cavity. This is explained in more detail in U.S. Pat. No. 8,303,664, issued Nov. 6, 2012, which is incorporated herein by reference in its entirety.

Figure 8:
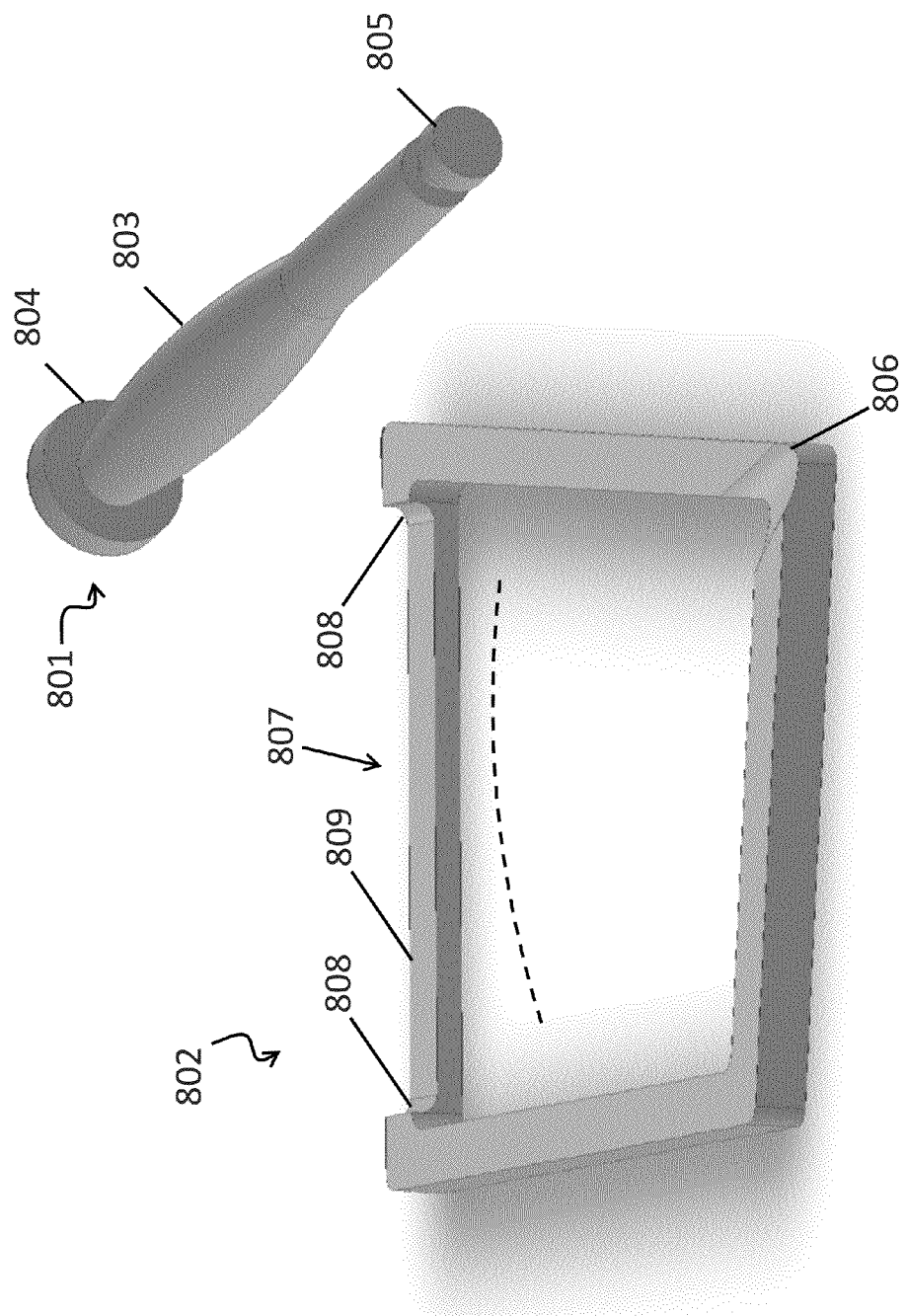
FIG. 8 schematically shows a cutting bit and guide for shaping a bone to receive a spacer for hemi-joint replacement.

FIG. 8 shows a bit 801 for cutting and a guide 802 for cutting a surface in a talonavicular joint. Unlike the bits in FIGS. 4 and 5, bit 801 cannot plunge cut. The cutting surface 803 can only cut perpendicular to the rotational axis of the bit 801. The cutting surface 803 can have end portions with radii of curvature $R_1$ and a central portion with a different radius of curvature $R_2$. The bit 801 includes an end collar 804 and a pivot collar 805. When the guide is secured to the bone and the bit 801 is seated on the guide 804, the pivot collar 805 sits in pivot groove 806 while the end collar 804 rides in the shaping groove 807. The shaping groove 807 can have end sections 808 with a radius of curvature $R_3$ while the central portion 809 can have a different radius of curvature $R_4$. The surface of the bone is prepared by swinging the bit 801 side to side, allowing the pivot collar 805 to remain essentially stationary in the pivot groove 806. The bit 801 moves vertically due to end collar 804 riding over the shaping groove 807. In some cases, $R_1$ equals $R_3$ so that the resulting prepared surface has a single radius of curvature around its perimeter. Because the bit 801 pivots, it necessarily sweeps out an arc. This is in contrast to the bits shown in FIGS. 4 and 5, which can be used with entirely rectilinear motion if desired. The resulting prepared surface of the bone will have differing radii of curvature in the cross-sections perpendicular to an axis, the same as described in reference to FIGS. 2, 6 and 7. But in this case, at least one axis is an arc, rather than a line. Such an arc is shown as a dashed arc in FIG. 8. Additionally, the because at least one axis is arcuate rather than a straight line, the cut surface and corresponding surface of the complementary implant will be stable against rolling about the arcuate axis even if cross sections perpendicular to the arcuate axis are curved with only a single radius of curvature.

In the case of FIG. 8, the cutting surface 803 defines one planar generating curve. Another generating curve is the arc through which the bit 801 and its cutting surface 803 is pivoted defines another generating curve. The resulting cut shape, in the simplest case where the bit pivots in a planar, circular arc, has an outline similar to a kidney bean, or cashew nut. In a radial cross-section, that is in a vertical plane that contains the axis of rotation of the bit, the surface has exactly the shape of the cutting surface 803, perhaps having two different radii of curvature. In an independent geometrical aspect, that is, in a cross-section lying in a vertical circular cylinder defined by the arc through which the bit 801 is pivoted, the curve defined by the surface is flat bottomed (an infinite radius of curvature) with rounded edges whose curvature is defined by the radius of the bit 801 (a finite, non-zero radius of curvature). In this way, the resulting surface can have non-constant radius of curvature in each of two geometrically independent aspects.

An additional level of complexity is added if further changes in curvature are added to the various aspects of the surface. As noted above, the shaping groove 807 can have multiple portions with different curvature in a vertical plane so that the collar 804 rides up and down as the bit 801 is pivoted. Additionally the shaping groove 807 can have radial curvature, so that as a user pivots the bit 801, in order to keep the collar 801 mated to the shaping groove 807, the bit 801 must move along its axis of symmetry through the pivot groove 806. The resulting shapes can have a wide variety of curvilinear independent geometrical aspects.

Figure 9:
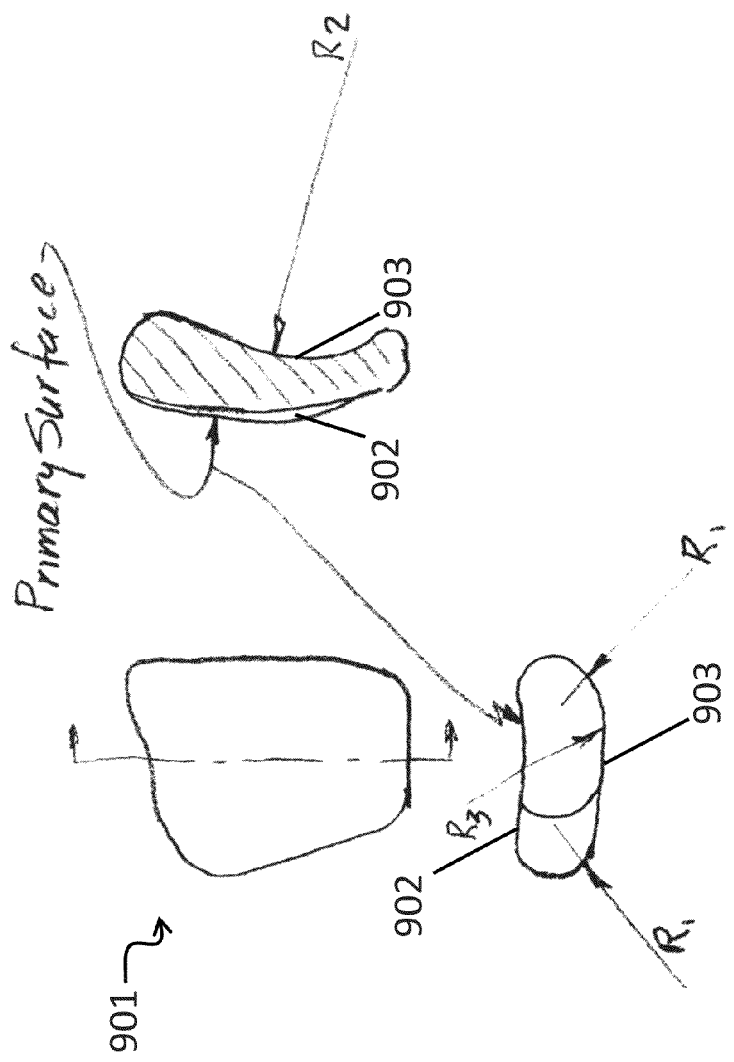
FIG. 9 schematically shows two views and a cross-section of a spacer for hemi-joint replacement in the talonavicular joint.

FIG. 9 shows an example of an implant 901 that could fit on the surface prepared by the bit 801 and guide 802 shown in FIG. 8. FIG. 9 shows a superior view of the implant looking down on to the articulating surface, a lateral elevation showing the perimeter portion of the stabilizing surface with radius of curvature $R_1$ and a central region with a convex radius of curvature $R_3$, and a cross-section in the coronal plane showing a concave radius of curvature $R_2$. In this example, the spacer has a saddle shaped articulating surface 902. The saddle shape can be seen in that the medial view of the spacer shows the articulating surface 902 as concave, while the coronal plane cross-section, which gives an anterior view, shows the articulating surface 902 as convex. Likewise, the stabilizing surface 903 is at least partially saddle shaped. The saddle shape can be seen in that the medial view of the spacer shows the stabilizing surface 903 as convex while the anterior view coronal-plane cross-section shows the stabilizing surface 903 as concave.

Figure 10:
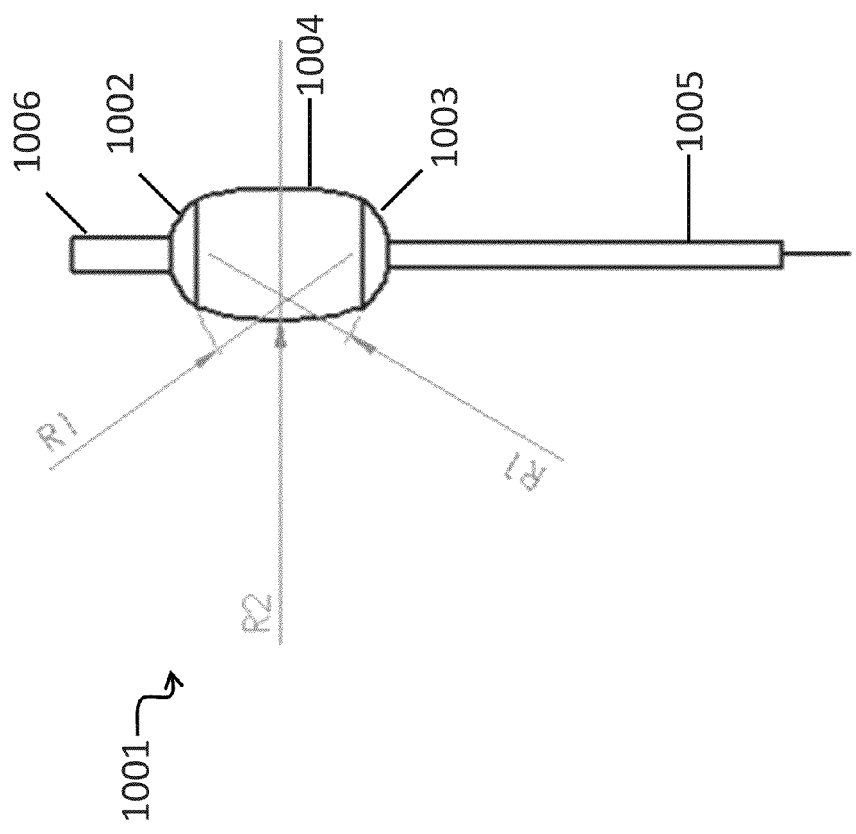
FIG. 10 schematically shows a bit for shaping a bone to receive a spacer for hemi-joint replacement.

FIG. 10 shows another bit 1001 for use with a pivot type of guide, similar to the guide 802 shown in FIG. 8. This bit 1001 has a more exaggerated difference between the different portions of the cutting surface. Perimeter portions 1002, 1003 are shown having radius of curvature $R_1$ while the central portion 1004 of the cutting surface has radius of curvature $R_2$. Like the other bits shown herein, the bit 1001 is fixedly attached to a drive shaft 1005. In this example, the drive shaft protrudes 1006 from the far side of the cutting surface to allow for the attachment of a collar at the far end if desired.

In many of the embodiments described herein, for example the embodiment shown in FIG. 5, a rotating drive shaft turns the bit while a collar or bushing of some kind surrounds the drive shaft. In some cases the collar rotates with the shaft, so that the rotating collar rides on a guide. In that case, the collar will need to be rotationally symmetric about the axis defined by the drive shaft. In other cases, the collar or bushing will not rotate with the drive shaft, but rather the drive shaft will rotate within the collar or bushing. In that case, the collar or bushing need not be rotationally symmetric, or symmetric at all.

Figure 11:
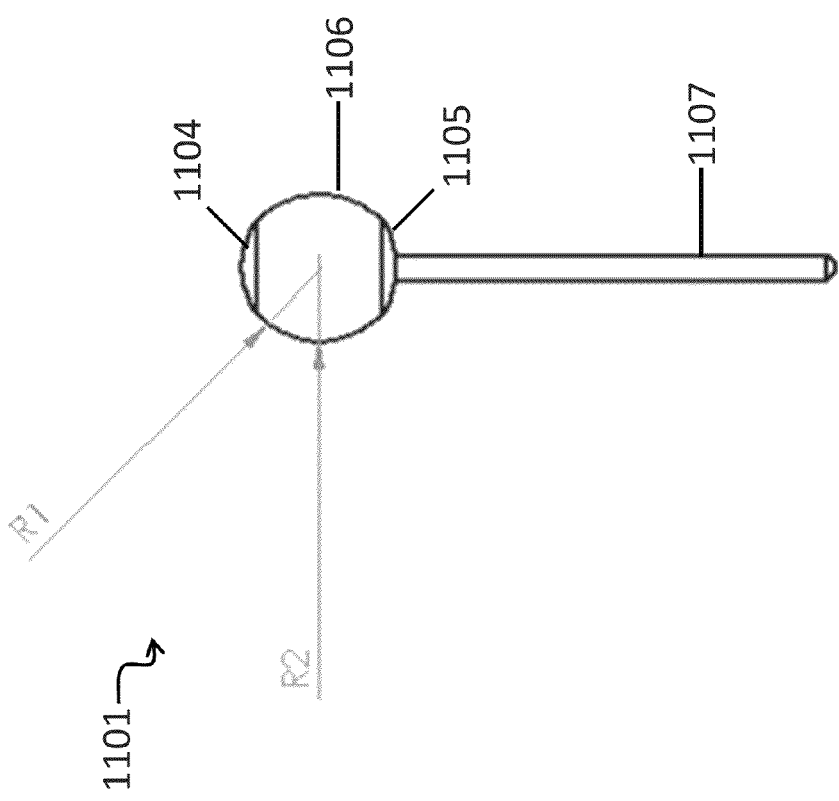

FIGS. 11, 12 and 13 schematically show a different combination of a bit 1101, a bushing 1102 and a mount 1103 to be used together to form a saddle shaped prepared surface on the bone. The bit 1101 is a side-cutting bit like those of FIGS. 8 and 10. The bit 1101 includes perimeter cutting portions 1104, 1105 defining a radius of curvature $R_1$ and a central cutting portion 1106 defining a radius of curvature $R_2$. The bit also includes a drive shaft 1107. Unlike the bits in FIGS. 8 and 10, bit 1101 has no protruding shaft on the far end of the bit from the drive shaft. The bit is designed without a built-in collar or bushing.

Instead, the bit 1101 is designed to spin in bushing 1102. FIG. 12 schematically shows three views of the bushing 1102. The bushing 1102 is generally arcuate in shape and an arc through the center of the bushing, shown as a dashed line, defines a radius of curvature $R_3$. The bushing 1102 defines a channel 1108 A channel 1108 through the bushing is sized to receive the drive shaft 1107 of the bit 1101.

FIG. 13 schematically shows a mount 1103 for use with the bit 1101 and bushing 1102. Clockwise from top left, FIG. 13 shows four views of the mount 1103: a top view; an angled perspective view showing, top, side and front; a side view; and a front view. The mount 1103 is to be attached to the bone where the surface will be prepared, and may be affixed, for example with screws or the like through the anchoring holes 1109. The mount defines a bushing slot 1110, sized and shaped to receive the bushing 1102, having the same arcuate shape and radius of curvature of the bushing 1102. In use, the bushing 1102 can slide side to side in the mount 1103. In some embodiments the rotating bit 1101 can slide front to back through the bushing, and the mount 1103 is deep enough in comparison to the bit 1101 that there is room to move the bit forward and backward. In other embodiments, the bit 1101 is roughly the same depth as the depth of the mount 1103 so that the bit only moves side to side. The mount can also define an entry slot 1111 through which the bit can be introduced into the cutting position inside the mount 1103.

The set-up shown in FIGS. 11-13, like the guide and bit in FIG. 8, can be used to create a stabilizing surface with curvilinear independent geometrical aspects, or it can be simplified to keep the independent geometrical aspects essentially rectangular. As shown, the bushing 1102 rides in bushing slot 1110 which is cut in to a curved front wall of the mount 1103. The bit 1101 must rotate as the bushing 1102 moves in the slot 1110 in order to keep the bushing 1102 fully seated. In some embodiments, the bushing 1102 may be constrained to so move, for example by a mating surface with the mount 1103, e.g., a tongue and groove or similar arrangement. Alternatively, if the mount 1103 had a flat front, the bit 1101 would not have to rotate at all to keep the bushing 1102 fully seated, and the resulting surface would have rectilinear independent geometrical aspects.

In any of the preceding examples, or in other embodiments, a kit comprising a bone-cutting bit and a guide can comprise a kit for cutting a prepared surface on a bone so as to be complementary to a particular spacer. A kit could include the spacer. A kit could include bushings and or collars necessary to generate a particular radius of curvature.

In any of the preceding examples, or in other embodiments, a kit comprising a bone-cutting bit and a guide can comprise a kit for cutting a prepared surface on a bone so as to be complementary to a particular spacer. A kit could include the spacer. A kit could include bushings and or collars necessary to generate a particular radius of curvature.

The joint to be partially replaced can be any synovial joint in the body. The disclosed devices and methods may be especially beneficial in small joints such as in the extremities. The joint can be in the foot, for example, the tibiotalar, talonavicular, metatarsal phalangeal, metatarsal tarsal, navicularcuneiform, calcaneal cuboid, subtalar, and interphalangeal (distal and proximal) joints. The joint can also be in the hand or wrist, for example, the carpometacarpal joint of the thumb, the scapho-trapezio-trapezoid (STT), the metacarpal-phalangeal joint of the thumb, and the proximal interphalangeal joints. Elbow, shoulder and knee joints may also be well suited to the disclosed methods and devices.

The combination of two or more generating curves with non-constant curvature can result in a wide variety of different surfaces and shapes, allowing the spacer and complementary surface to mimic a wide variety of bones and to function in a wide variety of joints. The resulting complementary surfaces on the bone and the spacer range from simple to complex. In various embodiments, the desired stability can be achieved with an implant whose stabilizing surface has at least three different curvatures distributed across two different axes or geometrically independent aspects. It should be understood that in general the goal of preparing a bone with such a surface is to allow the prepared surface to mate with a complementary stabilizing surface on a spacer, although one could prepare a bone with a cut surface for another purpose.

Any of the spacers described herein can be made of a variety of biocompatible materials, including pyrolytic carbon. In particular, the articulating and stabilizing surfaces may be formed entirely of pyrolytic carbon, as may be the bump, if the spacer includes one. Pyrolytic carbon has been used as an implant material for several decades in artificial heart valves and artificial joint implants. When used within a joint, the material exhibits extreme biocompatibility, surpassing common implant metals such as stainless steels, titanium alloys, ceramics, and cobalt chrome alloys. This extreme biocompatibility allows the body to act in two advantageous ways. First, pyrolytic carbon can transmit sliding motion under load to synovial joint surfaces while allowing the surfaces to remain healthy and functional over prolonged periods of time. Its biocompatibility against articular cartilage clinically surpasses all presently-known common implant metals. This property provides prolonged load bearing contact between the joint spacer and the remaining cartilage surface. The second advantage of pyrolytic carbon is its reaction in the presence of newly formed bone surfaces, such as are created when the end of a diseased bone is resected. In this case, pyrolytic carbon appears to encourage the formation of a new load transfer surface that responds favorably to small induced motions while transmitting joint loads. This property leads to the advantageous element of the claimed joint spacer, namely the absence of the need for rigid fixation between the spacer and the bone.

A spacer useful in hemi-joint replacement for replacing a removed portion of a first bone and articulating with a second bone can have an articulating surface and a stabilizing surface. The articulating surface can be sized and shaped to articulate with an articular surface of the second bone. The stabilizing surface can be sized and shaped to conform to a cut surface of the first bone. The spacer can define a first axis and a second axis not parallel to the first axis. The first and second axes may or may not be perpendicular. One or both axes can be lines or curves. In a cross-section of the spacer perpendicular to the first axis, the stabilizing surface defines a first curve. In a cross-section of the spacer perpendicular to the second axis, the stabilizing surface defines a second curve. The first curve can have a first portion with a first radius of curvature and a second portion with a second radius of curvature, where the first and second radii of curvature may be unequal. The second curve can have a third portion with a third radius of curvature and a fourth portion with a fourth radius of curvature, where the third and fourth radii of curvature may be unequal. Moreover, the second and fourth radii of curvature may be unequal as well.

The first and third radii of curvature may be equal to each other, and equal to the radius of curvature of a curved cutting blade of a bone shaving instrument. The second curve can further include a fifth portion with a fifth radius of curvature. The fifth radius of curvature can be unequal to both the third and fourth radii of curvature. The fifth radius of curvature could be, for example, infinite meaning that the fifth portion is substantially flat.

The stabilizing surface may include a bump, or protrusion, designed to sit inside a cavity defined by the prepared cut surface of the first bone. The bump would partially, but not entirely, fill the cavity so that, when the stabilizing surface is fully seated on the cut surface, the bump would protrude into the cavity. The movement of spacer on the cut surface could then be limited by the amount of movement possible by the bump in the cavity. Such arrangements are described in U.S. Pat. No. 8,303,664, which is incorporated herein by reference.

The stabilizing surface may be convex, concave, saddle-shaped, or a more complex combination of many radii of curvature. The perimeter of the spacer may be a circle, oval, ellipse, torus, trapezoid, parallelogram, kite, triangle, or any other shape that would help the spacer to mimic the anatomy of the replaced portion of bone. The exterior of the spacer may consist entirely, or essentially, of the articulating surface and the stabilizing surface, and no other, or essentially no other, surfaces. The first curve may consist entirely, or essentially, of the first and second portions, and may have no other, or essentially no other, portions. The same may be true for the second curve. Either the first or second axis, or both, may be curved.

The spacer can include pyrolytic carbon, can consist essentially of pyrolytic carbon, or can consist entirely of pyrolytic carbon. In particular, the articulating surface and/or the stabilizing surface may be formed of pyrolytic carbon.

Any such spacers may be included in a kit along with a bone-cutting bit having a cutting portion and a guide sized and shaped to guide the bone cutting bit. The bone-cutting bit and the guide can be sized and shaped such that, when the bone-cutting bit is guided by the guide, the cutting portion sweeps out a surface complimentary to the stabilizing surface of the spacer. A profile of the cutting portion can define a curve at least a portion of which has the first radius of curvature and a profile of the guide can define a curve at least a portion of which has the fourth radius of curvature. A profile of the cutting portion can be congruent to the first curve.

A joint that includes a first bone having a first articular surface and a second bone having a second articular surface can be distracted. The first bone can be prepared in at least two steps. First, the first bone may be prepared by removing the first articular surface, thereby creating a cut surface on the first bone, the cut surface defining a first axis and a second axis not parallel to the first axis. Second, the first bone may be prepared by shaping the cut surface so that: in a cross-section of the cut surface perpendicular to the first axis, the cut surface defines a first curve including a first portion with a first radius of curvature, and a second portion with a second radius of curvature not equal to the first radius of curvature; in a cross-section of the cut surface perpendicular to the second axis, the cut surface defines a second curve including a third portion with a third radius of curvature, and a fourth portion with a fourth radius of curvature not equal to the third radius of curvature; and the second and fourth radii of curvature are not equal. A spacer may be placed against the cut surface of the first bone, the spacer having an articulating surface sized and shaped to articulate with an articular surface of the second bone, and a stabilizing surface sized and shaped to be substantially complementary to the cut surface. The joint may be reapproximated such that the articulating surface of the spacer articulates with the second articular surface of the second bone, and the stabilizing surface of the spacer fully seats against the cut surface of the first bone.

A joint that includes a first bone having a first articular surface and a second bone having a second articular surface can be distracted. A spacer may be provided, the spacer having an articulating surface sized and shaped to articulate with an articular surface of the second bone, and a stabilizing surface a predetermined shape. The first bone can be prepared by removing the first articular surface of the first bone thereby creating a cut surface sized and shaped to be substantially complementary to the stabilizing surface. The spacer can be placed against the cut surface of the first bone with the stabilizing surface facing the complementary cut surface of the first bone. The joint can be reapproximated such that the articulating surface of the spacer articulates with the second articular surface of the second bone, and the stabilizing surface of the spacer fully seats against the cut surface of the first bone. The stabilizing surface can be defined by a combination of at least two surface-generating curves such that two geometrically independent aspects of the stabilizing surface are defined by non-constant curvature.

A spacer useful in hemi-joint replacement for replacing a removed portion of a first bone and articulating with a second bone can have an articulating surface and a stabilizing surface. The articulating surface can be sized and shaped to articulate with an articular surface of the second bone. The stabilizing surface can have a shape defined by a combination of at least two surface-generating curves such that two geometrically independent aspects of the stabilizing surface are defined by non-constant curvature. The two geometrically independent aspects can be rectilinear axes, which may or may not be perpendicular to one another. The two geometrically independent aspects can also be defined by a curvilinear coordinate system. Curvilinear coordinate systems include, for example polar, bipolar, parabolic, elliptic, hyperbolic, circular cylindrical, parabolic cylindrical, elliptic cylindrical, hyperbolic cylindrical, spherical, oblate spheroidal, prolate spheroidal, and toroidal coordinates. Any system in which geometrically independent aspects are defined in space can suffice.

Any such spacers may be included in a kit along with a bone-cutting bit having a cutting portion and a guide sized and shaped to guide the bone cutting bit. The bone-cutting bit and the guide can be sized and shaped such that, when the bone-cutting bit is guided by the guide, the cutting portion sweeps out a surface complimentary to the stabilizing surface of the spacer. A profile of the cutting portion can define one of the at least two surface-generating curves and a profile of the guide can define another of the at least two surface-generating curves.

The invention claimed is:

1. A method of using a kit, the kit comprising (a) a spacer for replacing a removed portion of a first bone and articulating with a second bone, (b) a bone-cutting bit having a cutting portion, and (c) a guide sized and shaped to guide the bone cutting bit, wherein:
    the spacer comprises:
        an articulating surface sized and shaped to articulate with an articular surface of the second bone; and
        a stabilizing surface sized and shaped to conform to a cut surface of the first bone, wherein:
            the spacer defines first axis and a second axis not parallel to the first axis;
            in a cross-section of the spacer perpendicular to the first axis, the stabilizing surface defines a first curve including:
                a first portion with a first radius of curvature; and
                a second portion with a second radius of curvature not equal to the first radius of curvature;
            in a cross-section of the spacer perpendicular to the second axis, the stabilizing surface defines a second curve including:
                a third portion with a third radius of curvature; and
                a fourth portion with a fourth radius of curvature not equal to the third radius of curvature; and
            the second and fourth radii of curvature are not equal; and
    the bone-cutting bit and the guide are sized and shaped such that, when the bone-cutting bit is guided by the guide, the cutting portion sweeps out a surface complimentary to the stabilizing surface of the spacer;
    wherein the method comprises:
    distracting a joint that comprises a first bone having a first articular surface and a second bone having a second articular surface;
    preparing the first bone by removing the first articular surface of the first bone by guiding the bone cutting bit with the guide, thereby creating a cut surface on the first bone complimentary to the stabilizing surface;
    placing the spacer with the stabilizing surface facing the complimentary cut surface of the first bone; and
    reapproximating the joint such that the articulating surface of the spacer articulates with the second articular surface of the second bone, and the stabilizing surface of the spacer fully seats against the cut surface of the first bone.

2. The method of claim 1 wherein the first and third radii of curvature are equal to each other and equal to the radius of curvature of the cutting portion of the bit.

3. The method of claim 1 wherein the second curve further includes a fifth portion with a fifth radius of curvature that is (a) not equal to the third radius of curvature and (b) not equal to the fourth radius of curvature.

4. The method of claim 3 wherein the fifth portion is substantially flat.

5. The method of claim 1 wherein the first axis is perpendicular to the second axis.

6. The method of claim 1 wherein the stabilizing surface is (a) convex, (b) concave, or (c) saddle-shaped.

7. The method of claim 1 wherein the perimeter of the spacer is substantially (a) elliptical, (b) circular, (c) trapezoidal, or (d) toroidal.

8. The method of claim 1 wherein the spacer further comprises a bump protruding from the stabilizing surface.

9. The method of claim 1 wherein the exterior of the spacer consists essentially of the stabilizing surface and the articulating surface.

10. The method of claim 1 wherein the first curve consists essentially of the first portion and the second portion.

11. The method of claim 1 wherein the first axis is curved.

12. The method of claim 1 wherein the spacer comprises pyrolytic carbon.

13. The method of claim 12 wherein the articulating surface and the stabilizing surface are formed entirely of pyrolytic carbon.

14. The method of claim 1 wherein the joint is a synovial joint.

15. The method of claim 14 wherein the joint is selected from the group consisting of the tibiotalar, talonavicular, metatarsal phalangeal, metatarsal tarsal, navicular cuneiform, calcaneal cuboid, subtalar, distal interphalangeal, and proximal interphalangeal joints.

16. The method of claim 1 wherein preparing the first bone comprises shaping the cut surface to be (a) convex, (b) concave, or (c) saddle-shaped.

17. The method of claim 1 wherein guiding the bone cutting bit with the guide comprises mating the guide with a collar that is attached to the bone cutting bit.

18. The method of claim 17 wherein the bone cutting bit is constrained to move along a single curve when the guide is mated to the collar.

19. The method of claim 17 wherein the bone cutting bit is constrained to move along a surface defined by two generating curves when the guide is mated to the collar.

* * * * *